United States Patent [19]
Krummel et al.

[11] Patent Number: 5,750,766
[45] Date of Patent: May 12, 1998

[54] PROCESS FOR THE PREPARATION OF ARYLMALONATES

[75] Inventors: Guenter Krummel, Vendersheim; Marcus Knell, Ingelheim, both of Germany

[73] Assignee: American Cyanamid Company, Madison, N.J.

[21] Appl. No.: 820,277

[22] Filed: Mar. 18, 1997

[51] Int. Cl.⁶ .................................................. C07C 69/76
[52] U.S. Cl. .................. 560/82; 560/80; 546/341
[58] Field of Search .................. 560/80, 82; 546/341

[56] References Cited

FOREIGN PATENT DOCUMENTS

| | | | |
|---|---|---|---|
| 0 550 113 A2 | 12/1991 | European Pat. Off. | C07D 487/04 |
| WO 94/20501 | 3/1993 | WIPO | C07D 487/04 |

*Primary Examiner*—Samuel Barts

[57] ABSTRACT

An effective and efficient process for the preparation of dialkyl arylmalonates of formula I,

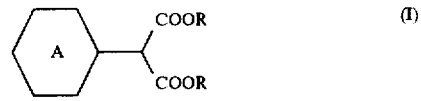

(ring A and R are defined in the specification). In this process, an arylmethylhalide of formula II

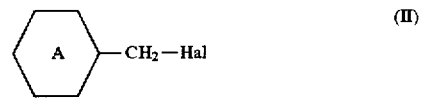

is treated with magnesium in an inert solvent, the resulting Grignard reagent is treated with a dialkyl carbonate or an alkyl chloroformiate, and the resulting reaction mixture is treated with a base.

12 Claims, No Drawings

PROCESS FOR THE PREPARATION OF ARYLMALONATES

BACKGROUND OF THE INVENTION

Arylmalonates are useful as intermediates for the preparation of a variety of compounds which are useful as agrochemicals, pharmaceuticals or liquid crystals. In particular, they are key intermediates in the preparation of fungicidal 6-aryltriazolopyrimidines which are described for example in EP 0 550 113 and WO 94/20501.

Conventionally the preparation of these compounds is carried in a 4-step synthesis starting from arylmethylhalides according to the following reaction scheme:

Scheme 1
Conventional process for the preparation of arylmalonates:

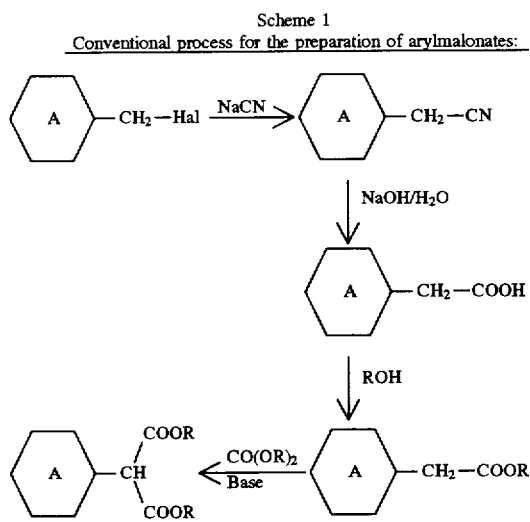

However, this method is not entirely satisfactory for large scale production, since highly toxic sodium cyanide is required and the overall yield of the reactions starting from arylmethylhalide is often low.

SUMMARY OF THE INVENTION

The present invention provides an effective and efficient process for the preparation of dialkyl arylmalonates of formula I,

wherein
ring A is an optionally substituted, optionally benzo-condensed phenyl group or an optionally substituted nitrogen containing 6-membered heteroaromatic group, and
R represents alkyl,
from an arylmethylhalide of formula II

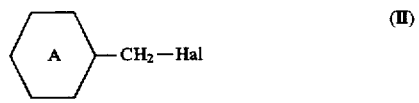

wherein
ring A has the meaning given for formula I, and
Hal represents halogen,
comprising the following steps:

(a) treating the arylmethylhalide of formula II with magnesium in an inert solvent,
(b) treating the resulting Grignard reagent with more than 2 moles of a dialkyl carbonate or an alkyl chloroformiate related to 1 mole of arylmethylhalide of formula II, and
(c) treating the resulting reaction mixture comprising an arylacetate of formula III.

wherein the ring A and R have the meaning given, and the dialkyl carbonate or the alkyl chloroformiate with a base.

It is, therefore, an object of the present invention to provide an efficient new process for the preparation of arylmalonates.

Other objects and advantages of the present invention will be apparent to those skilled in the art from the following description and the appended claims.

DETAILED DESCRIPTION OF THE PREFERRED EMBODIMENTS

In general terms, unless otherwise stated, as used herein the term halogen atom may denote a bromine, iodine, chlorine or fluorine atom, and is especially a bromine or chlorine atom.

Optionally substituted moieties may be unsubstituted or have from one up to the maximal possible number of substituents. Typically, 0 to 2 substituents are present.

In general terms, unless otherwise stated herein, the term alkyl as used herein with respect to a radical or moiety refer to a straight or branched chain radical or moiety. As a rule, such radicals have up to 10, in particular up to 6 carbon atoms. Suitably an alkyl moiety has from 1 to 6 carbon atoms, preferably from 1 to 3 carbon atoms. A preferred alkyl moiety is a methyl or especially an ethyl group.

In general terms, unless otherwise stated herein, the term optionally substituted or optionally benzo-condensed phenyl, as used herein with respect to a radical or moiety refers to an aryl group having 6 or 10 carbon atoms, preferably 6 carbon atoms, in particular phenyl being optionally substituted by one or more halogen atoms, nitro, cyano, alkyl, preferably $C_{1-6}$ alkyl, alkoxy, preferably $C_{1-6}$ alkoxy.

In general terms, unless otherwise stated herein, the term heteroaromatic group, as used herein with respect to a radical or moiety refers to a heteroaryl group having 6 ring atoms selected from carbon, nitrogen, oxygen and sulphur, at least one of which being nitrogen.

In a preferred embodiment

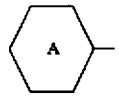

denotes

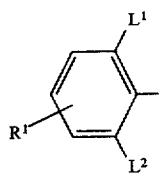

in which
L¹ and L² each independently represent a halogen atom, preferably fluorine or chlorine, and
R¹ represent a hydrogen or halogen atom or an alkyl or alkoxy group.

In a particularly preferred embodiment ring A represents 2-chloro-6-fluorophenyl.

Further preferred embodiments of the process according to the present invention is a process wherein:

the magnesium used in step (a) is activated with 1,2-dibromoethane (DBE) or diethylether (DEE);

1.1 to 3.5 moles magnesium, preferably 1.3 to 3.1 moles magnesium related to 1 mole of arylmethylhalide of formula II are used in step (a);

the reaction of step (a) is carried out in the presence of an inert solvent selected from the group consisting of diethylether (DEE), dimethoxymethane (DMM), tert-butylmethylether (MTBE), tetrahydropyran (THP), diisopropylether (DIP), toluene (TOL) and mesitylene (MES), or a mixture of these solvents;

the reaction of step (a) is carried out in the presence of a tertiary amine, in particular tri-n-butylamine (TBA);

the reaction of step (a) is carried out at temperatures between 0° C. and 100° C., preferably between 25° C. and 50° C.;

in step (b) the Grignard reagent is treated with 4 to 12 moles of the dialkyl carbonate, in particular diethyl carbonate (DEC), or with 4 to 12 moles of the alkyl chloroformiate, in particular ethyl chloroformiate (ECF), related to 1 mole of arylmethylhalide of formula II;

the reaction of step (b) is carried out at temperatures between −80° C. and 20° C., preferably −40° C. to 0° C., in particular −30° C. to −5° C.;

the reaction mixture obtained in step (b) is treated with a diluted aqueous acid and the organic phase comprising the arylacetate of formula III and the dialkyl carbonate or the alkyl chloroformiate is separated from the aqueous layer;

the reaction of step (c) is carried out with 1.1 to 3.0 moles of the base related to 1 mole of arylmethylhalide of formula II;

the reaction of step (c) is carried out at temperatures between 80° C. and 160° C.

As a rule, the initiation of the Grignard formation requires a long time in solvents like DMM, therefore activation with DEE or DBE yields more reproducible results. Preferably a mixture of the arylmethylhalide and the solvent is slowly added to a mixture of magnesium, the solvent and 0.005 to 0.02 mol of the activator related to 1 mole of the arylmethylhalide.

Since, as a rule, an excess of magnesium is used, the remaining magnesium can be used as activ bottom in the following reaction without further activation.

Most preferred the reaction of steps (a) and (b) is carried out in mixtures of solvents and or activators, in particular in mixtures essentially consisting of:

TBME or DMM and DBE or DEE, as rule 1000 parts of TBME or DMM to 0.5–2.0 parts or DBE; or toluene, DEE and TBA.

During the reaction of step (b) it is favourable to avoid that an excess of the Grignard reagent is present, in order to prevent the formation of ketons as a side reaction according to reaction scheme 2:

Scheme 2
Formation of ketons:

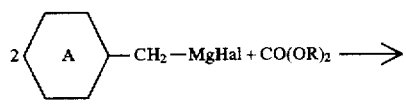

Therefore, the reaction mixture comprising the Grignard reagent is prefearbly added to the dialkyl carbonate or the alkyl chloroformiate which are used in excess.

As a rule the reaction between the Grignard reagent and the dialkyl carbonate or the alkyl chloroformiate is carried out at low temperatures, preferably below 0° C., in particular between −10° C. and −25° C.

Under these preferred reaction conditions the post-reaction is as a rule completed within 0.5 to 48, preferably 1 to 10 hours.

In principle, it is possible to treat the arylactate formed in step (b) with the base in a one-pot synthesis, i.e. by adding the base to the reaction mixture. However, the inorganic salts present in this reaction mixture require the use of an high excess of the base in order to trap the halide ions present.

Therefore, the reaction mixture obtained in step (b) preferably is neutralized with a diluted acid, in order to remove the inorganic salts.

Then the base is added to the separated organic layer, preferably after the solvent has been partly distilled off.

Preferred bases are metal alkoxides, in particular sodium alkoxides as for example sodium methoxide or sodium ethoxide.

After addition of the base, as a rule, the reaction mixture is heated and the alkanol formed from the dialkyl carboxylate is distilled off. The remaining reaction mixture preferably is neutralized with diluted acid, the phases are separated and the organic layer is dried and concentrated.

The crude product obtained can be purified according to standard methods for example by distillation in vacuo, chromatographic methods or crystallization.

However, the crude product obtained according to the process of this invention is pure enough to be used as intermediate without further purification.

In order to facilitate a further understanding of the invention, the following illustrative examples are presented. The invention is not limited to the specific embodiments described or illustrated, but encompasses the full scope of the appended claims.

EXAMPLE 1

Preparation of diethyl 2-chloro-6-fluorophenylmalonate

A mixture of magnesium (27 g), dimethoxymethane (40 ml) and dibromoethane (0.5 ml) is heated to 43° C. under stirring. After 5 minutes a mixture of 2-chloro-6-fluorobenzylchloride (4 g) and dimethoxymethane (16 ml) is added to initiate the reaction and stirred for 20 minutes. Within 2 hours a mixture of 2-chloro-6-fluorobenzylchloride (96 g) and dimethoxymethane (384 ml) is dosed to the reaction mixture under stirring at 42° to 44° C. The mixture is kept under reflux with stirring for 1.5 hours.

Upon cooling down to 30° C. the reaction mixture is dosed to diethoxycarbonate (340 ml) at −8° to −14° C. within 0.5 hours. The reaction mixture is held at −10° C. for 2 hours. Upon warming up to 1° C. the reaction mixture is neutralized with a mixture of concentrated HCl (60 ml) and water (150 ml). The phases are separated and the organic phase is transferred to another reactor.

The reaction mixture is concentrated by distillation. Sodium ethylate (46 g) is added after cooling down to 75° C. The reaction mixture is heated to 120° C. and the remaining dimethoxymethane and the formed ethanol is distilled off. Upon cooling down to 20° C. the reaction mixture is neutralized with a mixture of concentrated HCl (60 ml) and water (150 ml).

The phases are separated and the organic phase is dried with magnesium sulfate and concentrated in vacuo to yield the crude product (128 g /80% yield).

EXAMPLES 2 to 15

Preparation of diethyl 2-chloro-6-fluorophenylmalonate

Analogously to example 1 2-chloro-6-fluorobenzylchloride (CFBC) is treated with magnesium, a carbonylation reagent and sodium ethylate as base in different solvents and at different temperatures.

The relative amounts of the reactands and solvents, the reaction temperature of the carbonylation step and yields are shown in the following table I:

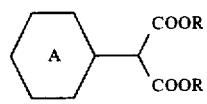

(I)

wherein ring A is an optionally substituted, optionally benzo-condensed phenyl group or an optionally substituted nitrogen containing 6-membered heteroaromatic group, and R represents alkyl, from an arylmethylhalide of formula II

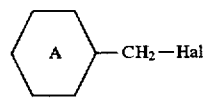

(II)

wherein ring A has the meaning given for formula I, and

Hal represents halogen, the improvement wherein is that (a) the arylmethylhalide of formula II is treated with magnesium in an inert solvent, (b) the resulting Grignard reagent is treated with more than 2 moles of a dialkyl carbonate or an alkyl chloroformiate related to 1 mole of arylmethylhalide of formula II, and (c) the resulting reaction mixture comprising an arylacetate of formula III,

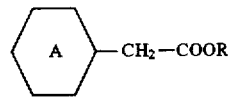

(III)

wherein the ring A and R have the meaning given, and the dialkyl carbonate or the alkyl chloroformiate is treated with a base.

TABLE I

| | | | | | | Examples 2 to 15 | | |
|---|---|---|---|---|---|---|---|---|
| Example | Initiator | Solvent | Mg/CFBC | Carbonyl-ation agent | Carbonylation agent/CFBC | NaOEt/CFBC | temperature (°C.) | Yield (%) |
| 2 | DBE | TBA | 5 | DEC | 5 | 1.8 | −10 | 31 |
| 3 | DBE | DMM | 2 | DEC | 5 | 1.5 | −10 | 75 |
| 4 | DEE | MTBE | 2 | DEC | 5 | 1.8 | −10 | 75 |
| 5 | DEE | TBA/TOL | 2 | DEC | 5 | 2.4 | −10 | 53 |
| 6 | DBE | DMM | 2 | ECF | 5 | 2.4 | −10 | 66 |
| 7 | DBE | DMM | 2 | ECF | 5 | 1.2 | 20 | 48 |
| 8 | DBE | DMM | 3 | DEC | 10 | 2.5 | −28 | 91 |
| 9 | DBE | DMM | 3 | DEC | 10 | 2.5 | −25 | 90 |
| 10 | DBE | DMM | 2 | DEC | 10 | 2 | −25 | 61 |
| 11 | DBE | DMM | 2.5 | DEC | 5 | 1.2 | −10 | 80 |
| 12 | DEE | DMM | 3 | DEC | 6 | 2.5 | −5 | 80 |
| 13 | DBE | DEE | 2 | DEC | 11 | 1.6 | −25 | 67 |
| 14 | DBE | DMM/TBA | 2.5 | DEC | 5 | 1.6 | −10 | 64 |
| 15 | DEE | MES | 2 | DEC | 5 | 2.5 | −10 | 81 |

What is claimed is:

1. In an improved process for the preparation of dialkyl arylmalonates of formula I, 2. A process according to claim 1, wherein the magnesium used in step (a) is activated with 1,2-dibromoethane or diethylether.

3. A process according to claim 1, wherein 1.1 to 3.5 moles magnesium related to 1 mole of arylmethylhalide of formula II are used in step (a).

4. A process according to claim 1, wherein the reaction of step (a) is carried out in the presence of an inert solvent selected from the group consisting of diethylether, dimethoxymethane, tert-butylmethylether, tetrahydropyran, diisopropylether, toluene and mesitylene, or a mixture of these solvents.

5. A process according to claim 4, wherein the reaction of step (a) is carried out in the presence of a tertiary amine.

6. A process according to claim 1, wherein the reaction of step (a) is carried out at temperatures between 0° C. and 100° C.

7. A process according to claim 1, wherein in step (b) the Grignard reagent is treated with 4 to 12 moles of the dialkyl carbonate or with 4 to 12 moles of the alkyl chloroformiate related to 1 mole of arylmethylhalide of formula II.

8. A process according to claim 1, wherein the reaction of step (b) is carried out at temperatures between −80° C. and 20° C.

9. A process according to claim 1, wherein the reaction mixture obtained in step (b) is treated with a diluted aqueous acid and the organic phase comprising the arylacetate of formula III and the dialkyl carbonate or the alkyl chloroformiate is separated from the aqueous layer.

10. A process according to claim 1, wherein the reaction mixture obtained in step (b) is treated with an alkali metal alkoxide.

11. A process according to claim 1, wherein the reaction of step (c) is carried out with 1.1 to 3.0 moles of the base related to 1 mole of arylmethylhalide of formula II.

12. A process according to claim 1, wherein the reaction of step (c) is carried out at temperatures between 80° C. and 160° C.

* * * * *